United States Patent [19]

Yonan

[11] 4,217,306
[45] Aug. 12, 1980

[54] α-ARYL-α,α-BIS[ω-(DISUBSTITUTED AMINO)ALKYL]-ACETAMIDES

[75] Inventor: Peter K. Yonan, Morton Grove, Ill.

[73] Assignee: G. D. Searle & Co., Skokie, Ill.

[21] Appl. No.: 940,527

[22] Filed: Sep. 8, 1978

Related U.S. Application Data

[60] Continuation-in-part of Ser. No. 901,949, May 1, 1978, Pat. No. 4,153,797, which is a division of Ser. No. 776,563, Mar. 11, 1977, Pat. No. 4,107,205.

[51] Int. Cl.$^2$ .................. C07C 103/20; C07C 103/19; A61K 31/16; A61K 31/165
[52] U.S. Cl. ........................... 260/557 R; 260/558 A; 260/465 E; 424/320; 424/324
[58] Field of Search ...................... 260/558 A, 557 R

[56] References Cited

U.S. PATENT DOCUMENTS

| | | | |
|---|---|---|---|
| 2,884,436 | 4/1959 | Janssen et al. | 260/558 A X |
| 2,894,955 | 7/1959 | Aspergren et al. | 260/558 A X |
| 3,022,302 | 2/1962 | Martensson et al. | 260/247.7 |
| 3,022,314 | 2/1962 | Aspergren et al. | 260/558 A X |
| 3,078,275 | 2/1963 | Moffett et al. | 260/558 A X |
| 3,225,091 | 12/1965 | Ainsworth et al. | 260/558 A |
| 3,344,146 | 9/1967 | Casadio | 260/558 A X |

FOREIGN PATENT DOCUMENTS 673495 12/1965 Belgium .
689347 4/1967 Belgium .
6405327 11/1964 Netherlands .

OTHER PUBLICATIONS

Stenseth et al., J. Org. Chem. 34 (10), 3007–3010 (1969).
Pala et al., J. Med. Chem. 16 (6), 720–723 (1973).
Casadio et al., J. Med. Chem. 9 (5), 707–714 (1966), 8 (5), 594–598 (1965).
Borovicka et al., CA 52:5335i (1958).
Blicke et al., J. Am. Chem. Soc., 75, 4334–4335 (1953).

Primary Examiner—Thomas A. Waltz
Attorney, Agent, or Firm—Dragan J. Karadzic; Albert Tockman

[57] ABSTRACT

Novel α-aryl-α,α-bis[ω-(disubstituted amino)alkyl-acetamides are described herein. The compounds are useful as anti-arrhythmic agents. The compounds are prepared by reacting an appropriate disubstituted acetonitrile with an appropriate haloalkyl amine and subsequently hydrolyzing the resulting nitrile with concentrated sulfuric acid.

12 Claims, No Drawings

α-ARYL-α,α-BIS[ω-(DISUBSTITUTED AMINO)ALKYL]-ACETAMIDES

This application is a continuation-in-part of application Ser. No. 901,949, filed May 1, 1978, now U.S. Pat. No. 4,153,797, which is a division of application Ser. No. 776,563, filed Mar. 11, 1977, now U.S. Pat. No. 4,107,205.

The present invention relates to α-aryl-α,α-bis[ω-(disubstituted amino)alkyl]acetamides having the following general formula

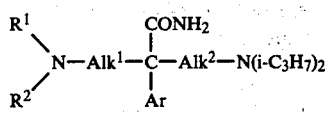

wherein $R^1$ is lower alkyl having from 1 to 7 carbon atoms or cycloalkyl having 5 or 6 carbon atoms; $R^2$ is lower alkyl having from 1 to 7 carbon atoms; or $R^1$ and $R^2$ together with the N-atom represents an azamonocyclic ring which may contain further heteroatom and which is optionally substituted with 1 or 2 phenyl or lower alkyl having from 1 to 4 carbon atoms; Ar is pyridyl, phenyl, trifluoromethylphenyl, biphenylyl, phenyl substituted with 1 or 2 halogen or lower alkyl having from 1 to 4 carbon atoms, 1- or 2-naphthyl optionally substituted with halogen or lower alkyl having from 1 to 4 carbon atoms, or cycloalkyl having from 3 to 6 carbon atoms optionally substituted with lower alkyl having from 1 to 4 carbon atoms, or cyclohexyl and $Alk^1$ and $Alk^2$ are independently alkylene radicals having from 2 to 4 carbon atoms.

The lower alkyls having from 1 to 7 carbon atoms contemplated in the foregoing formula are methyl, ethyl, propyl, butyl, pentyl, hexyl, heptyl and the branched-chain isomers thereof.

The lower alkyls having from 1 to 4 carbon atoms contemplated in the foregoing formula are methyl, ethyl, propyl, butyl and the branched-chain isomers thereof, with methyl being preferred.

The alkylene radicals having from 2 to 4 carbon atoms contemplated in the foregoing formula are 1,2-ethanediyl, 1-methyl-1,2-ethanediyl, 1,1-dimethyl-1,2-ethanediyl, 1,2-propanediyl, 2-methyl-1,3-propanediyl, 1,4-butanediyl, or like bivalent, saturated, acyclic, straight- or branched-chain, hydrocarbon radicals.

The halogens contemplated in the foregoing formula are fluorine, chlorine, bromine and iodine, with fluorine and chlorine being preferred.

Positioning of the phenyl substituents relative to the point of attachment of the phenyl or, where two are present, to each other is not critical. Thus, within the scope of this invention are o-, m-, or p-monosubstituted phenyls of the type described above, such as o-fluorophenyl, m-chlorophenyl, p-fluorophenyl, p-tolyl and m-trifluoromethylphenyl; and 2,3-, 2,4-, 2,5-, 2,6-, 3,4-, and 3,5-disubstituted phenyls of the type described above, such as 2,4-dichlorophenyl, 2,6-dichlorophenyl, 2,3-difluorophenyl, 3,4-dichlorophenyl, 3-chloro-5-fluorophenyl and 2-fluoro-5-methylphenyl.

The cycloalkyls having 5 or 6 carbon atoms contemplated in the foregoing formula are cyclopentyl and cyclohexyl.

The cycloalkyls having from 3 to 6 carbon atoms contemplated in the foregoing formula are cyclopropyl, cyclobutyl, cyclopentyl and cyclohexyl, with cyclohexyl being preferred.

Within the scope of this invention are halogen and lower alkyl substituted naphthyls and cycloalkyls of the type described above. Positioning of these substituents relative to the point of attachment of the naphthyl or cycloalkyl radical is not critical.

The azamonocyclic rings contemplated in the foregoing formula contain from 4 to 6 carbon atoms and are exemplified by piperidine, pyrrolidine, 1H-hexahydroazapine, piperazine and morpholine, with piperidine being preferred. These azamonocyclic rings can be substituted with 1 or 2 phenyl or lower alkyl of the type described above. Positioning of these substituents relative to the point of attachment of the azamonocyclic ring, or, where two are present, to each other is not critical.

Equivalent to the foregoing bases for the purposes of this invention are non-toxic pharmacologically acceptable acid addition salts thereof having the formula

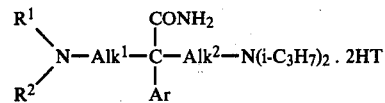

wherein $R^1$, $R^2$, Ar, $Alk^1$, and $Alk^2$ are as previously defined; and T represents 1 equivalent of an anion—for example, fluoride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate, ascorbate, benzoate, cinnamate or the like—which, in combination with the cationic portion of a salt aforesaid, is neither biologically nor otherwise incompatible.

More specifically, the present invention relates to α-aryl-α,α-bis[ω-(disubstituted amino)alkyl]acetamides of the formula

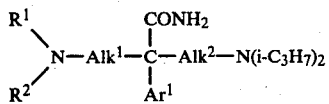

and the non-toxic pharmacologically acceptable acid addition salts thereof; wherein $R^1$, $R^2$, $Alk^1$ and $Alk^2$ are as previously defined, and $Ar^1$ is biphenylyl, 1- or 2-naphthyl optionally substituted with halogen or lower alkyl having from 1 to 4 carbon atoms, or cycloalkyl having from 3 to 6 carbon atoms optionally substituted with lower alkyl having from 1 to 4 carbon atoms or cyclohexyl.

Compounds of the present invention of the formula

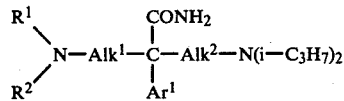

and the non-toxic pharmacologically acceptable acid addition salts thereof; wherein $R^1$ is lower alkyl having from 1 to 7 carbon atoms or cycloalkyl having 5 or 6 carbon atoms; $R^2$ is lower alkyl having from 1 to 7 carbon atoms; $Ar^1$ is biphenylyl, 1- or 2-naphthyl optionally substituted with halogen or lower alkyl having from 1 to 4 carbon atoms, or cycloalkyl having from 3 to 6 carbon atoms optionally substituted with lower alkyl having from 1 to 4 carbon atoms or cyclohexyl; and Alk$^1$ and Alk$^2$ are independently alkylene radicals having from 2 to 4 carbon atoms are preferred embodiments and of these embodiments compounds in which Ar$^1$ is 4-biphenylyl are further preferred.

Another preferred embodiment of this invention are compounds of the formula

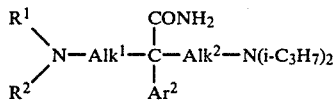

and the non-toxic pharmacologically acceptable acid addition salts thereof; wherein R$^1$ is lower alkyl having from 1 to 7 carbon atoms or cycloalkyl having 5 or 6 carbon atoms; R$^2$ is lower alkyl having from 1 to 7 carbon atoms; Ar$^2$ is 1- or 2-naphthyl optionally substituted with halogen or lower alkyl having from 1 to 4 carbon atoms; and Alk$^1$ and Alk$^2$ are independently alkylene radicals having from 2 to 4 carbon atoms, and of these embodiments compounds in which Ar$^2$ is 1- or 2-naphthyl are further preferred.

Another preferred embodiment of this invention are compounds of the formula

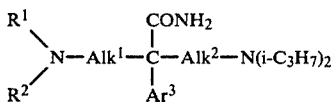

and the non-toxic pharmacologically acceptable acid addition salts thereof; wherein R$^1$ is lower alkyl having from 1 to 7 carbon atoms or cycloalkyl having 5 or 6 carbon atoms; R$^2$ is lower alkyl having from 1 to 7 carbon atoms; Ar$^3$ is cycloalkyl having from 3 to 6 carbon atoms optionally substituted with lower alkyl having from 1 to 4 carbon atoms or cyclohexyl; and Alk$^1$ and Alk$^2$ are independently alkylene radicals having from 2 to 4 carbon atoms, and of these embodiments compounds in which Ar$^3$ is cyclohexyl or cyclohexyl substituted with cyclohexyl or lower alkyl having from 1 to 4 carbon atoms are further preferred.

Another preferred embodiment of this invention are compound of the formula

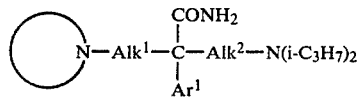

and the non-toxic pharmacologically acceptable acid addition salts thereof; wherein Ar$^1$ is biphenylyl, 1- or 2-naphthyl optionally substituted with halogen or lower alkyl having from 1 to 4 carbon atoms, or cycloalkyl having from 3 to 6 carbon atoms optionally substituted with lower alkyl having from 1 to 4 carbon atoms or cyclohexyl; Alk$^1$ and Alk$^2$ are independently alkylene radicals having from 2 to 4 carbon atoms, and

is morpholino, 1-piperazinyl optionally substituted with lower alkyl having from 1 to 4 carbon atoms, or a group

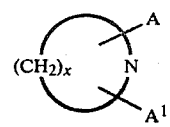

wherein A and A$^1$ are independently hydrogen, phenyl or lower alkyl having from 1 to 4 carbon atoms; and x is positive integer from 4 to 6 inclusive.

Another preferred embodiment of this invention are compounds of the formula

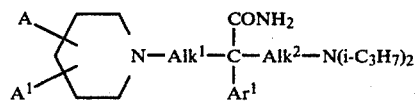

and the non-toxic pharmacologically acceptable acid addition salts thereof; wherein Ar$^1$ is biphenylyl, 1- or 2-naphthyl optionally substituted with halogen or lower alkyl having from 1 to 4 carbon atoms, or cycloalkyl having from 3 to 6 carbon atoms optionally substituted with lower alkyl having from 1 to 4 carbon atoms or cyclohexyl; Alk$^1$ and Alk$^2$ are independently alkylene radicals having from 2 to 4 carbon atoms; and A and A$^1$ are independently hydrogen, phenyl or lower alkyl having from 1 to 4 carbon atoms, and of these embodiments compounds in which Ar$^1$ is 4-biphenylyl are further preferred.

Another preferred embodiment of this invention are compounds of the formula

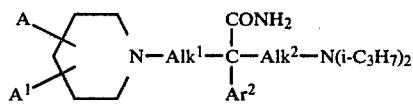

and the non-toxic pharmacologically acceptable acid addition salts thereof; wherein Ar$^2$ is 1- or 2-naphthyl optionally substituted with halogen or lower alkyl having from 1 to 4 carbon atoms; Alk$^1$ and Alk$^2$ are independently alkylene radicals having from 2 to 4 carbon atoms; and A and A$^1$ are independently hydrogen, phenyl or lower alkyl having from 1 to 4 carbon atoms, and of these embodiments compounds in which Ar$^2$ is 1- or 2-naphthyl are further preferred.

Another preferred embodiment of this invention are compounds of the formula

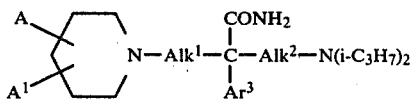

and the non-toxic pharmacologically acceptable acid addition salt thereof; wherein Ar$^3$ is cycloalkyl having from 3 to 6 carbon atoms optionally substituted with lower alkyl having from 1 to 4 carbon atoms or cyclohexyl; Alk$^1$ and Alk$^2$ are independently alkylene radicals having from 2 to 4 carbon atoms; and A and A$^1$ are independently hydrogen, phenyl or lower alkyl having from 1 to 4 carbon atoms, and of these embodiments compounds in which $Ar^3$ is cyclohexyl optionally substituted with cyclohexyl or lower alkyl having from 1 to 4 carbon atoms are further preferred.

Another preferred embodiment of this invention are compounds of the formula

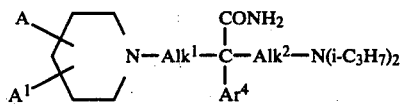

and the non-toxic pharmacologically acceptable acid addition salts thereof; wherein $Ar^4$ is phenyl optionally substituted with 1 or 2 halogen or lower alkyl having from 1 to 4 carbon atoms; $Alk^1$ and $Alk^2$ are independently alkylene radicals having from 2 to 4 carbon atoms; A is hydrogen, phenyl, or lower alkyl having from 1 to 4 carbon atoms; and $A^2$ is phenyl or lower alkyl having from 1 to 4 carbon atoms.

The compounds of this invention are useful because of their pharmacological properties. In particular, they possess activity as anti-arrhythmic agents. Thus, they bring about a return to normal heart rhythm in animals in which the heart rhythm has been irregular.

The anti-arrhythmic activity of the present compounds has been demonstrated in the following way. Ventricular arrhythmia is induced by a 2-stage ligation of the anterior decending branch of the left coronary artery in each of 2 or more dogs. Quantities of test compound (5 mg/kg) are administered intravenously at intervals to a possible maximum accumulated dose of 20 mg/kg. A compound is rated active if it produces at least 25% reduction in ectopic beats for a period of at least 10 minutes in half or more of the dogs tested.

A further test demonstrating the anti-arrhythmic utility of the present compounds is as follows:

Male mongrel dogs are connected to a physiograph to follow heart and blood action. At the onset of the testing, an initial dose of 40 mcg/kg ouabain is administered intravenously in a saline solution. This is followed 30 minutes later by a dose of 20 mcg/kg of ouabain and, at 15 minute intervals, by a dose of 10 mcg/kg of ouabain until ventricular arrhythmia occurs and persists for 20 minutes. Then, a saline solution of test compound is administered at a dose of 5 mg/kg. If the heart action does not become normal, additional test compound is administered at a dose of 5 mg/kg at 15 minute intervals until heart action becomes normal or until the total dose of test compound administered is 20 mg/kg. The procedure is run in two or more dogs. A compound is considered active if it causes a return to normal heart action for a period of 15 minutes or more in half or more of the dogs tested at a dose of 20 mg/kg or less.

Among the compounds of this invention which have been found active in these tests are representative compounds α-(4-biphenylyl)-α,α-bis[2-(diisopropylamino)ethyl]acetamide, α,α-bis[2-(diisopropylamino)ethyl]-α-(1-naphthyl)acetamide, α,α-bis[2-(diisopropylamino)ethyl]-α-(2-naphthyl)acetamide, α-cyclohexyl-α,α-bis[2-(diisopropylamino)ethyl]acetamide, α-(4-biphenylyl)-α-[2-(diisopropylamino)ethyl]-α-(2-piperidinoethyl)acetamide, α,α-bis[2-(diisopropylamino)ethyl]-α-(1-naphthyl)acetamide, α,α-bis[2-(diisopropylamino)ethyl]-α-(2-naphthyl)acetamide, α-(o-fluorophenyl)-α-[2-(diisopropylamino)ethyl]-α-[2-(2-methyl-1-piperidinyl)ethyl]acetamide, and α-(o-fluorophenyl)-α-[2-(diisopropylamino)ethyl]-α-[2-(2,6-dimethyl-1-piperidinyl)ethyl]acetamide.

The compounds of this invention are conveniently prepared by reacting disubstituted acetonitrile of the formula

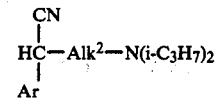

wherein Ar and $Alk^2$ are as previously defined with a haloalkyl amine of the formula

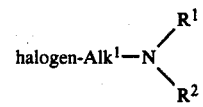

wherein $R^1$, $R^2$, and $Alk^1$ are as previously defined and halogen is preferably chlorine, in the presence of a strong base such as sodium amide in an inert solvent such as toluene with heating and subsequently hydrolyzing the resultant nitrile of the formula

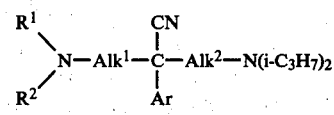

wherein $R^1$, $R^2$, Ar, $Alk^1$, and $Alk^2$ are as previously defined; with concentrated sulfuric acid.

In an alternate procedure for the preparation of the present compounds in which $R^1$ and $R^2$ are both isopropyl, and $Alk^1$ and $Alk^2$ are alike alkylene having from 2 to 4 carbon atoms, monosubstituted acetonitrile of the formula

wherein Ar is as previously defined, is reacted with two molar equivalents of a haloalkyl amine of the formula

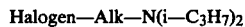

wherein Alk is alkylene having from 2 to 4 carbon atoms and halogen is preferably chlorine, in the presence of a strong base such as sodium amide in an inert solvent such as toluene with heating and the resultant nitrile of the formula

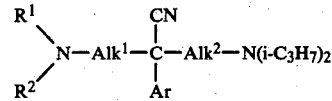

wherein $R^1$, $R^2$, Ar, $Alk^1$, and $Alk^2$ are as previously defined; is subsequently hydrolyzed with concentrated sulfuric acid.

The intermediate nitriles of the formula

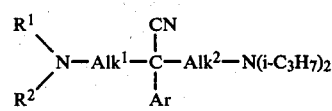

wherein R¹, R², Ar, Alk¹, and Alk² are as previously defined, can also be conveniently prepared using the phase transfer technique. The phase transfer technique involves thorough stirring of the disubstituted acetonitrile of the formula

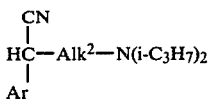

wherein Ar and Alk² are as previously defined with a haloalkyl amine of the formula

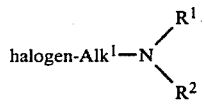

wherein R¹, R², and Alk¹ are as previously defined and halogen is preferably chlorine in a mixture of an inert organic solvent and 40-50% sodium hydroxide in the presence of about 1% by weight of an ammonium salt such as benzyltriethylammonium chloride, benzyltriethylammonium bromide, benzyltrimethylammonium chloride and benzyltrimethylammonium bromide. This reaction can also be run without the organic solvent but in the presence of 40-50% sodium hydroxide. The reaction time is not critical and can vary from several hours to several days.

The invention will appear more fully from the examples which follow. These examples are given by way of illustration only and are not to be construed as limiting the invention either in spirit or in scope as many modifications both in materials and in methods will be apparent from this disclosure to those skilled in the art. In these examples, temperatures are given in degrees Centigrade (°C.) and quantities of materials in parts by weight unless parts by volume is specified. The relationship between parts by weight and parts by volume is the same as that existing between grams and milliliters.

EXAMPLE 1

The solution of 100 parts of α-(4-biphenylyl)acetonitrile and 90 parts of 2-chloro-N,N-diisopropylethylamine in 850 parts by volume of toluene is heated to about 80° C. and then 22 parts of sodium amide is added slowly over a period of 30 minutes keeping the temperature at 80°-85° C. The mixture is heated at 80° C. for another 30 minutes and then cooled to room temperature. 500 Parts by volume of water is then added to the mixture and the organic layer is separated and extracted with dilute hydrochloric acid. The aqueous acidic extract is made alkaline by the addition of dilute sodium hydroxide. The alkaline mixture is extracted with ether and the ether extract is dried over calcium sulfate, filtered and stripped of solvent to afford an oil which solidifies upon standing. The crude oil is crystallized from hexane to afford α-(4-biphenylyl)-α-[2-(diisopropylamino)ethyl]acetonitrile, melting at about 54°-56° C. This compound is represented by the following structural formula

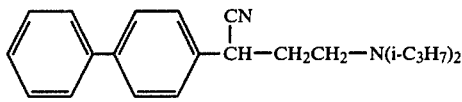

EXAMPLE 2

Method A

The solution of 19 parts of α-(4-biphenylyl)acetonitrile and 25 parts of 2-chloro-N,N-diisopropylethylamine in 100 parts by volume of toluene is heated to about 80° C. and then 11 parts of sodium amide is added over a period of 30 minutes keeping the temperature at 80°-85° C. The temperature is then raised to about 105° C. and another 25 parts of 2-chloro-N,N-diisopropylethylamine in 100 parts by volume of toluene is added over a period of 20 minutes. The reaction mixture is heated for another hour at 105°-110° C. and then cooled to room temperature when 200 parts by volume of water is added. The organic layer is separated and extracted with dilute hydrochloric acid. The aqueous acidic extract is made alkaline by the addition of dilute sodium hydroxide, extracted with ether and the ether extract dried over calcium sulfate, filtered and the solvent evaporated to afford α-(4-biphenylyl)-α,α-bis[2-(diisopropylamino)ethyl]acetonitrile, as a low melting solid. This compound is represented by the following structural formula

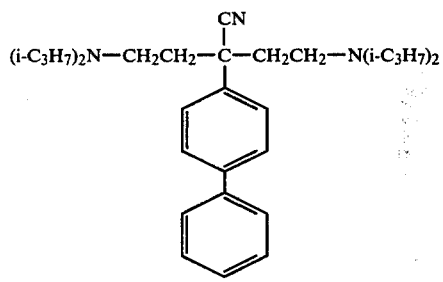

Method B

To a solution of 16 parts of α-(4-biphenylyl)-α-[2-(diisopropylamino)ethyl]acetonitrile in 150 parts by volume of toluene is added 2.7 parts of sodium amide and the solution is heated over a period of 15 minutes at about 100° C. Then 13 parts of 2-chloro-N,N-diisopropylethylamine in 40 parts by volume of toluene is added slowly over a period of 20 minutes. This mixture is heated at 100°-105° C. for about 90 minutes and then cooled to room temperature when 150 parts by volume of water is added. The organic layer is separated, dried over calcium sulfate, filtered and the solvent evaporated to afford α-(4-biphenylyl)-α,α-bis[2-(diisopropylamino)ethyl]acetonitrile, as a low melting solid. This compound is identical with the compound of Example 2, Method A.

EXAMPLE 3

The mixture of 50 parts of α-(4-biphenylyl)acetonitrile, 45.8 parts of 2-chloro-N,N-diisopropylethylamine, 80 parts by volume of 50% sodium hydroxide, 250 parts by volume of methylene chloride and 1 part of benzyltrimethylammonium bromide is stirred at room temperature with slight cooling in an icy water bath for about 24 hours. The mixture is then poured into water and to this mixture additional quantity of methylene chloride is added. The organic layer is separated, washed with water, dried over anhydrous sodium sulfate and concentrated to afford α-(4-biphenylyl)-α-[2-(diisopropylamino)ethyl]acetonitrile, as a solid. This compound is identical to that of Example 1.

The mixture of 18.75 parts of the above compound, 10.8 parts of 2-chloro-N,N-diisopropylethylamine, 54 parts by volume of methylene chloride, 30 parts by volume of 50% sodium hydroxide and catalytic amount of benzyltrimethylammonium bromide is stirred at room temperature for about 48 hours and then poured into water. To the resultant mixture additional quantity of methylene chloride is added and the organic layer separated. The organic layer is washed with water, dried over anhydrous sodium sulfate, filtered and the solvent evaporated to afford α-(4-biphenylyl)-α,α-bis[2-(diisopropylamino)ethyl]acetonitrile, as a solid. This compound is identical to that of Example 2.

EXAMPLE 4

17.5 Parts of α-(4-biphenylyl)-α,α-[2-(diisopropylamino)ethyl]acetonitrile is dissolved in a solution of 48 parts by volume of concentrated sulfuric acid, 48 parts by volume of glacial acetic acid and 24 parts by volume of water. The resultant solution is heated on a steam bath for about 21 hours. The solution is then cooled to about 0° C. and made alkaline by the addition of dilute sodium hydroxide. The alkaline solution is extracted with ether, the ether extract dried over calcium sulfate, filtered and stripped of solvent to afford α-(4-biphenylyl)-α,α-bis[2-(diisopropylamino)ethyl]acetamide, melting at about 110°–111° C. after recrystallization from hexane. This compound has the following structural formula

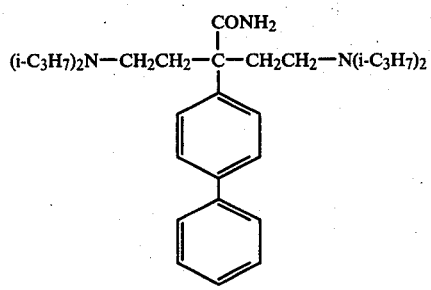

EXAMPLE 5

To a solution of 10 parts of α-(4-biphenylyl)-α,α-bis[2-(diisopropylamino)ethyl]acetamide in 350 parts by volume of ether is added dropwise with stirring 2 molar equivalents of hydrochloric acid in isopropyl alcohol. The mixture is stirred for about 2 hours when the resulting salt is separated by filtration to afford α-(4-biphenylyl)-α,α-bis[2-(diisopropylamino)ethyl]acetamide dihydrochloride, as a solid.

EXAMPLE 6

Substitution of an equivalent quantity of 1-(2-chloroethyl)piperidine for 2-chloro-N,N-diisopropylethylamine called for in Example 2, Method B affords, by the procedure there detailed, α-(4-biphenylyl)-α-[2-(diisopropylamino)ethyl]-α-(2-piperidinoethyl)acetonitrile, as a low melting solid.

When an equivalent quantity of the above acetonitrile is substituted in the procedure of Example 4, there is obtained α-(4-biphenylyl)-α-[2-(diisopropylamino)ethyl]-α-(2-piperidinoethyl)acetamide, as a solid melting at about 156°–157° C. after crystallization from hexane. This compound has the following structural formula

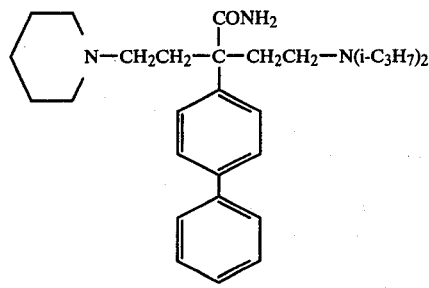

EXAMPLE 7

Substitution of an equivalent quantity of 2-chloro-N,N-dimethylethylamine for 2-chloro-N,N-diisopropylethylamine called for in Example 2, Method B affords by the procedure there detailed, α-(4-biphenylyl)-α-[2-(diisopropylamino)ethyl]-α-[2-(dimethylamino)-ethyl]acetonitrile, as an oil.

When an equivalent quantity of the above acetonitrile is substituted in the procedure of Example 4, there is obtained α-(4-biphenylyl)-α-[2-(diisopropylamino)ethyl]-α-(2-(dimethylamino)ethyl]acetamide, as a solid melting at about 123°–124° C. after crystallization from pentane. This compound has the following structural formula

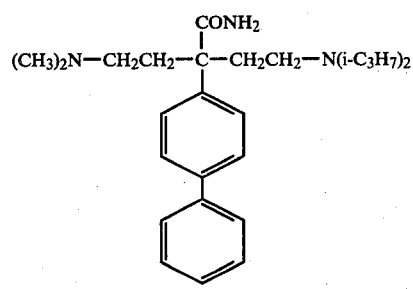

EXAMPLE 8

Substitution of an equivalent quantity of 1-naphthylacetonitrile for α-(4-biphenylyl)acetonitrile called for in Example 1 affords by the procedure there detailed, α-[2-(diisopropylamino)ethyl]-α-(1-naphthyl)acetontrile, as a solid melting at about 45° C. after crystallization from hexane.

Substitution of an equivalent quantity of the above acetonitrile for α-[4-biphenylyl]-α-[2-(diisopropylamino)ethyl]acetonitrile called for in Example 2, Method B, affords α,α-bis[2-(diisopropylamino)ethyl]-α-(1-naphthyl)acetonitrile, as an oil.

When an equivalent quantity of the preceding acetonitrile is substituted in the procedure of Example 4, there is obtained α,α-bis[2-(diisopropylamino)ethyl]-α-(1-naphthyl)acetamide, as a solid melting at about 163°–165° C. after crystallization from a mixture of ether and hexane. This compound has the following structural formula

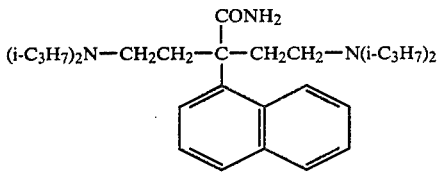

EXAMPLE 9

Substitution of an equivalent quantity of 2-naphthylacetonitrile for α-(4-biphenylyl)acetonitrile called for in Example 1 affords by the procedure there detailed, α-[2-(diisopropylamino)ethyl]-α-(2-naphthyl)acetonitrile, as a solid.

Substitution of an equivalent quantity of the above acetonitrile for α-(4-biphenylyl)-α-[2-(diisopropylamino)ethyl]acetonitrile called for in Example 2, Method B affords α,α-bis[2-(diisopropylamino)ethyl]-α-(2-naphthyl)acetonitrile as an oil.

When an equivalent quantity of the preceding acetonitrile is substituted in the procedure of Example 4, there is obtained α,α-bis[2-(diisopropylamino)ethyl]-α-(2-naphthyl)acetamide, as a solid melting at about 120°–121° C. after crystallization from hexane. This compound has the following structural formula

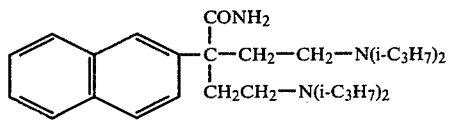

EXAMPLE 10

Substitution of equivalent quantities of α-[2-(diisopropylamino)ethyl]-α-(1-naphthyl)acetonitrile and 1-(2-chloroethyl)piperidine for α-(4-biphenylyl)-α-[2-(diisopropylamino)ethyl]acetonitrile and 2-chloro-N,N-diisopropylethylamine called for in Example 2, Method B, respectively affords α-[2-(diisopropylamino)ethyl]-α-(1-naphthyl)-α-(2-piperidinoethyl)acetonitrile, as an oil.

When an equivalent quantity of the preceding acetonitrile is substituted in the procedure of Example 4, there is obtained α-[2-(diisopropylamino)ethyl]-α-(1-naphthyl)-α-(2-piperidinoethyl)acetamide, as a solid melting at about 127°–129° C. after crystallization from pentane. This compound has the following structural formula

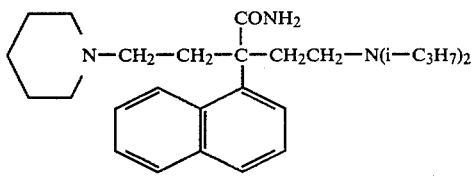

EXAMPLE 11

Substitution of equivalent quantities of α-[2-(diisopropylamino)ethyl]-α-(2-naphthyl)acetonitrile and 1-(2-chloroethyl)-piperidine for α-(4-biphenylyl)-α-[2-(diisopropylamino)ethyl]acetonitrile and 2-chloro-N,N-diisopropylethylamine called for in Example 2, Method B, respectively affords α-[2-(diisopropylamino)ethyl]-α-(2-naphthyl)-α-(2-piperidinoethyl)acetonitrile, as an oil.

Substitution of an equivalent quantity of the preceding acetonitrile in the procedure of Example 4, affords α-[2-(diisopropylamino)ethyl]-α-(2-naphthyl)-α-(2-piperidinoethyl)acetamide, as a solid melting at about 169°–170° C. after crystallization from hexane. This compound has the following structural formula

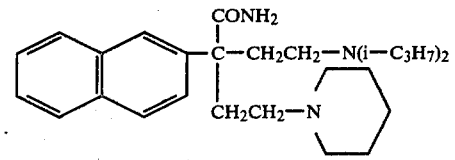

EXAMPLE 12

Substitution of equivalent quantities of α-(o-fluorophenyl)-α-[2-(diisopropylamino)ethyl]acetonitrile and 1-(2-chloroethyl)-2-methylpiperidine in the procedure of Example 2, Method B and substantial repetition of the procedure detailed therein, affords α-(o-fluorophenyl)-α-[2-(diisopropylamino)ethyl]-α-[2-(2-methyl-1-piperidinyl)ethyl]acetonitrile, as an oil boiling at about 170°–175° C. at 0.5 mm. pressure.

7 Parts of the preceding acetonitrile is dissolved in a solution of 67 parts by volume of concentrated sulfuric acid and 3 parts by volume of water. The resulting solution is heated on a steam bath for about 2 hours and then cooled to about 0° C. and made alkaline by the addition of diluted sodium hydroxide. The alkaline solution is extracted with ether, the ether extract dried over calcium sulfate, stripped of solvent and the residue crystallized from pentane to afford α-(o-fluorophenyl)-α-[2-(diisopropylamino)ethyl]-α-[2-(2-methyl-1-piperidinyl)ethyl]acetamide, melting at about 90°–91° C. This compound has the following structural formula

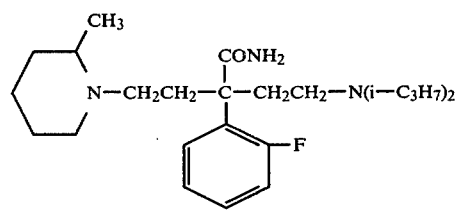

EXAMPLE 13

Substitution of equivalent quantities of α-(o-fluorophenyl)-α-[2-(diisopropylamino)ethyl]acetonitrile and 1-(2-chloroethyl)-2,6-dimethylpiperidine in the procedure of Example 2, Method B, and substantial repetition of the procedure detailed therein, affords α-(o-fluorophenyl)-α-[2-(diisopropylamino)ethyl]-α-[2-(2,6-dimethyl-1-piperidinyl)ethyl]acetonitrile, as an oil boiling at about 170°–175° C. at 0.3 mm. pressure.

Substitution of the preceding acetonitrile in Example 12, second paragraph, and substantial repetition of the procedure detailed therein, affords α-(o-fluorophenyl)-α-[2-(diisopropylamino)ethyl]-α-[2-(2,6-dimethyl-1-piperidinyl)ethyl]acetamide, melting at about 102°–103° C. after crystallization from hexane. This compound has the following structural formula

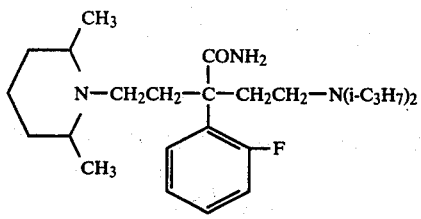

EXAMPLE 14

Substitution of an equivalent quantity of 1-(2-chloroethyl)-4-phenylpiperidine for 2-chloro-N,N-diisopropylethylamine called for in Example 2, Method B, and substantial repetition of the procedure detailed therein, affords α-(4-biphenylyl)-α-[2-(diisopropylamino)ethyl]-α-[2-(4-phenyl-1-piperidinyl)ethyl]acetonitrile.

When an equivalent quantity of the above acetonitrile is substituted in the procedure of Example 4, there is obtained α-(4-biphenylyl)-α-[2-(diisopropylamino)ethyl]-α-[2-(4-phenyl-1-piperidinyl)ethyl]acetamide.
This compound is represented by the following structural formula

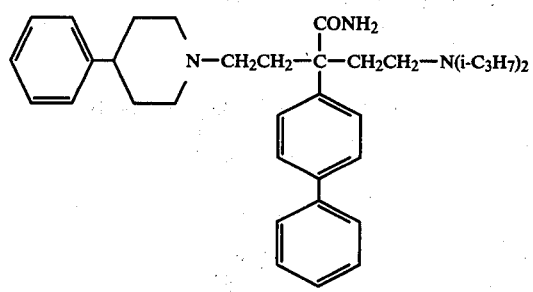

EXAMPLE 15

Substitution of equivalent quantities of α-[2-(diisopropylamino)ethyl]-α-(1-naphthyl)acetonitrile and 1-(2-chloroethyl)-4-phenylpiperidine for α-(4-biphenylyl)-α-[2-(diisopropylamino)ethyl]acetonitrile and 2-chloro-N,N-diisopropylethylamine called for in Example 2, Method B, respectively and substantial repetition of the procedure detailed therein, affords α-[2-(diisopropylamino)ethyl]-α-(1-naphthyl)-α-[2-(4-phenyl-1-piperidinyl)ethyl]acetonitrile.

When an equivalent quantity of the above acetonitrile is substituted in the procedure of Example 4, there is obtained α-[2-(diisopropylamino)ethyl]-α-(1-naphthyl)-α-[2-(4-phenyl-1-piperidinyl)ethyl]acetamide. This compound is represented by the following structural formula

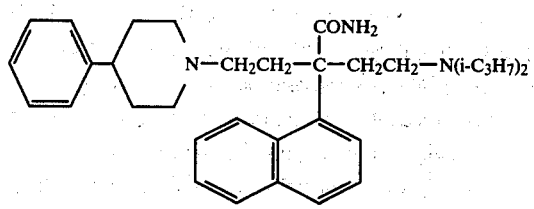

EXAMPLE 16

A solution of 100 parts of 1-bromo-2-methylnaphthalene, 80.5 parts of N-bromosuccinimide and 0.5 part of benzoyl peroxide in 1500 parts by volume of carbon tetrachloride is heated at reflux temperature for several hours. The solution is then cooled, washed twice with water and the organic layer separated. The organic layer is dried over calcium sulfate, filtered and concentrated to give 1-bromo-2-(bromomethyl)naphthalene, as an oil which solidifies on standing.

A mixture of 99 parts of 1-bromo-2-(bromomethyl)naphthalene, 103 parts of potassium cyanide and 1 part of benzyl triethylammonium chloride in 150 parts by volume of methylene chloride and 30 parts by volume of water is stirred at room temperature for about 72 hours. The mixture is then diluted with additional quantities of methylene chloride and water, the organic layer separated, dried over calcium sulfate, and concentrated to give α-(1-bromo-2-naphthyl)acetonitrile, as a solid.

69 Parts of α-(1-bromo-2-naphthyl)acetonitrile is stirred in 150 parts by volume of 50% sodium hydroxide and then 0.7 parts of benzyltriethylammonium chloride is added to the mixture. To this mixture is added slowly a solution of 41.82 parts of 2-chloro-N,N-diisopropylethylamine in 150 parts by volume of methylene chloride and the resulting mixture is stirred at room temperature for about 2 hours. Then, additional quantities of methylene chloride and water are added to the reaction mixture. The organic layer is then separated, dried over anhydrous sodium sulfate and concentrated to give α-(1-bromo-2-naphthyl)-α-[2-(diisopropylamino)ethyl]acetonitrile, as a solid. This compound is represented by the following structural formula

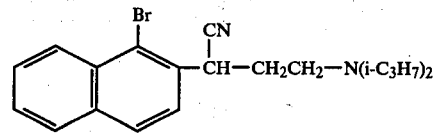

EXAMPLE 17

Substitution of equivalent quantities of α-(1-bromo-2-naphthyl)-α-[2-(diisopropylamino)ethyl]acetonitrile and 1-(2-chloroethyl)piperidine in the procedure of Example 2, Method B affords α-(1-bromo-2-naphthyl)-α-[2-(diisopropylamino)ethyl]-α-(2-piperidinoethyl)acetonitrile, as an oil.

When an equivalent quantity of the above nitrile is substituted in the procedure of Example 4, there is obtained α-(1-bromo-2-naphthyl)-α-[2-(diisopropylamino)ethyl]-α-(2-piperidinoethyl)acetamide.
This compound is represented by the following structural formula

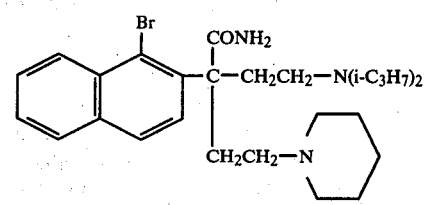

EXAMPLE 18

Substitution of equivalent quantities of α-[2-(diisopropylamino)ethyl]-α-phenylacetonitrile and 2-chloro-N,N-diisopropylpropylamine in the procedure of Example 2, Method B affords, after chromatographic separation α-[2-(diisopropylamino)ethyl]-α-[2-(diisopropylamino)-1-methylethyl]-α-phenylacetonitrile and α-[2-(diisopropylamino)ethyl]-α-[2-(diisopropylamino)-2-methylethyl]-α-phenylacetonitrile.

EXAMPLE 19

When an equivalent quantity of α-[2-(diisopropylamino)ethyl]-α-[2-(diisopropylamino)-1-methylethyl]-α-phenylacetonitrile is substituted in the procedure of Example 12, second paragraph, there is obtained α-[2-(diisopropylamino)ethyl]-α-[2-(diisopropylamino)-1-methylethyl]-α-phenylacetamide. This compound is represented by the following structural formula

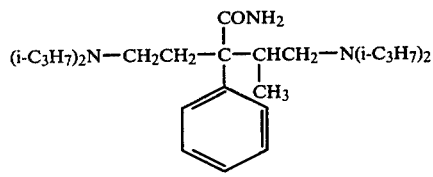

EXAMPLE 20

When an equivalent quantity of α-[2-(diisopropylamino)ethyl]-α-[2-(diisopropylamino)-2-methylethyl]-α-phenylacetonitrile is substituted in the procedure of Example 12, second paragraph, there is obtained α-[2-(diisopropylamino)ethyl]-α-[2-(diisopropylamino)-2-methylethyl]-α-phenylacetamide. This compound is represented by the following structural formula

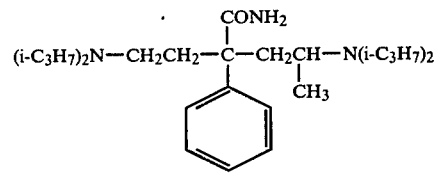

EXAMPLE 21

Substitution of an equivalent quantity of α-(4-biphenylyl)-α-[2-(diisopropylamino)ethyl]acetonitrile for α-[2-(diisopropylamino)ethyl]-α-phenylacetonitrile called for in Example 18 and substantial repetition of the procedure detailed therein, affords, after chromatographic separation, α-(4-biphenylyl)-α-[2-(diisopropylamino)ethyl]-α-[2-(diiso-propylamino)-1-methylethyl]acetonitrile and α-(4-biphenylyl)-α-[2-(diisopropylamino)ethyl]-α-[2-(diisopropylamino)-2-methylethyl]acetonitrile.

EXAMPLE 22

When an equivalent quantity of α-(4-biphenylyl)-α-[2-(diisopropylamino)ethyl]-α-[2-(diisopropylamino)-1-methylethyl]acetonitrile is substituted in the procedure of Example 12, second paragraph, there is obtained α-(4-biphenylyl)-α-[2-(diisopropylamino)ethyl]-α-[2-(diisopropylamino)-1-methylethyl]acetamide having the following structural formula

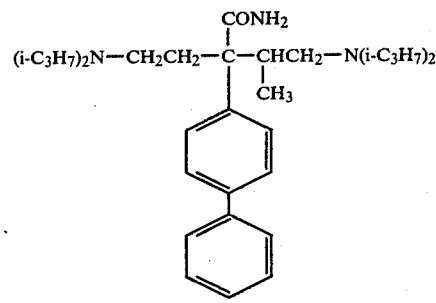

EXAMPLE 23

When an equivalent quantity of α-(4-biphenylyl)-α-[2-(diisopropylamino)ethyl]-α-[2-(diisopropylamino)-2-methylethyl]acetonitrile is substituted in the procedure of Example 12, second paragraph, there is obtained α-(4-biphenylyl)-α-[2-(diisopropylamino)ethyl]-α-[2-(diisopropylamino)-2-methylethyl]acetamide having the following structural formula

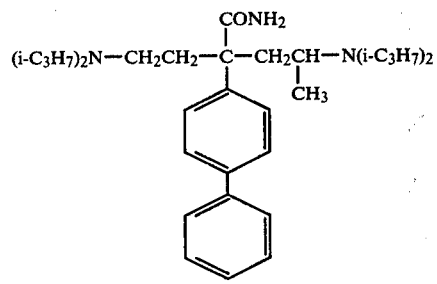

EXAMPLE 24

Substitution of an equivelent quantity of α-[2-(diisopropylamino)ethyl]-α-(1-naphthyl)acetonitrile for α-[2-(dissopropylamino)ethyl]-α-phenylacetonitrile called for in Example 18 and substantial repetition of the procedure detailed therein, affords, after chromatographic separation, α-[2-(diisopropylamino)ethyl]-α-[2-(diisopropylamino)-1-methylethyl]-α-(1-naphthyl)acetonitrile and α-[2-diisopropylamino)ethyl]-α-[2-(diisopropylamino)-2-methylethyl]-α-(1-naphthyl)acetonitrile.

EXAMPLE 25

When an equivalent quantity of α-[2-(diisopropylamino)ethyl]-α-[2-(diisopropylamino)-1-methylethyl]-α-(1-naphthyl)acetonitrile is substituted in the procedure of Example 4, there is obtained α-[2-(diisopropylamino)ethyl]-α-[2-(diisopropylamino)-1-methylethyl]-α-(1-naphthyl)acetamide, having the following structural formula

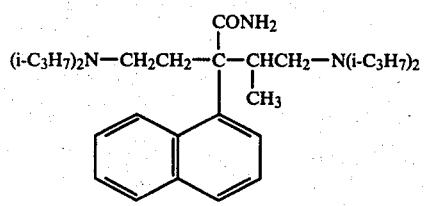

EXAMPLE 26

When an equivalent quantity of α-[2-(diisopropylamino)ethyl]-α-[2-(diisopropylamino)-2-methylethyl]-α-(1-naphthyl)acetonitrile is substituted in the procedure of Example 4, there is obtained α-[2-(diisopropylamino)ethyl]α-[2-(diisopropylamino)-2-methylethyl]-α-(1-naphthyl)acetamide, having the following structural formula

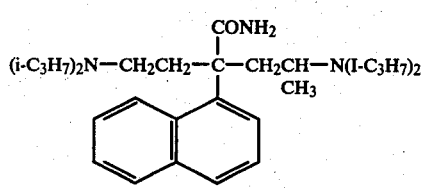

EXAMPLE 27

Substitution of equivalent quantities of α-(4-biphenylyl)-α-[2-(diisopropylamino)ethyl]acetonitrile and 2-chloro-N-cyclohexyl-N-methylethylamine in the procedure of Example 2, Method B, there is obtained α-(4-biphenylyl)-α-[2-(diisopropylamino)ethyl]-α-[2-(N-cyclohexyl-N-methylamino)ethyl]acetonitrile.

When an equivalent quantity of the preceding acetonitrile is substituted in the procedure of Example 4, there is obtained α-(4-biphenylyl)-α-[2-diisopropylamino)ethyl]-α-[2-(N-cyclohexyl-N-methylamino)ethyl]acetamide. This compound has the following structural formula

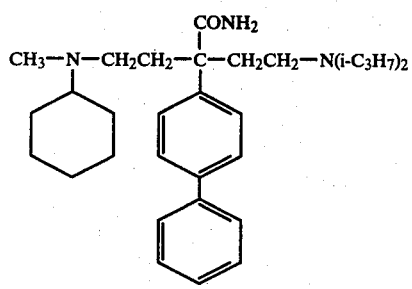

EXAMPLE 28

Substitution of equivalent quantities of α-(4-biphenylyl)-α-[2-(diisopropylamino)ethyl]acetonitrile and 1-(2-chloroethyl)pyrrolidine in the procedure of Example 2, Method B, affords α-(4-biphenylyl)-α-[2-(diisopropylamino)ethyl]-α-(2-pyrrolidinoethyl)acetonitrile.

When an equivalent quantity of the preceding acetonitrile is substituted in the procedure of Example 4, there is obtained α-(4-biphenylyl)-α-[2-(diisopropylamino)ethyl]-α-(2-pyrrolidinoethyl)acetamide. This compound has the following structural formula

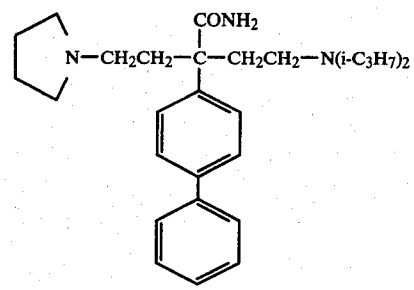

EXAMPLE 29

Substitution of equivalent quantities of α-(2-methyl-1-naphthyl)-α-[2-(diisopropylamino)ethyl]acetonitrile and 1-(2-chloropropyl)piperidine in the procedure of Example 2, Method B, affords, after chromatographic separation α-[2-(diisopropylamino)ethyl]-α-(2-methyl-1-naphthyl)-α-[1-methyl-2-(1-piperidinyl)ethyl]acetonitrile and α-[2-(diisopropylamino)ethyl]-α-(2-methyl-1-naphthyl)-α-[2-methyl-2-(1-piperidinyl)ethyl]acetonitrile.

EXAMPLE 30

When an equivalent quantity of α-[2-(diisopropylamino)ethyl]-α-(2-methyl-1-naphthyl)-α-[1-methyl-2-(1-piperidinyl)ethyl]acetonitrile is substituted in the procedure of Example 4, there is obtained α-[2-(diisopropylamino)ethyl]-α-(2-methyl-1-naphthyl)-α-[1-methyl-2-(1-piperidinyl)ethyl]acetamide. This compound has the following structural formula

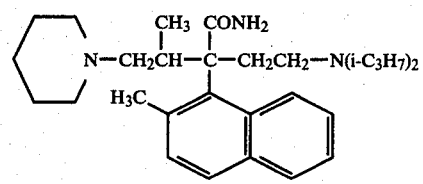

EXAMPLE 31

When an equivalent quantity of α-[2-(diisopropylamino)ethyl]-α-(2-methyl-1-naphthyl)-α-[2-methyl-2-(1-piperidinyl)ethyl]acetonitrile is substituted in the procedure of Example 4, there is obtained α-[2-(diisopropylamino)ethyl]-α-(2-methyl-1-naphthyl)-α-[2-methyl-2-(1-piperidinyl)ethyl]acetamide. This compound has the following structural formula.

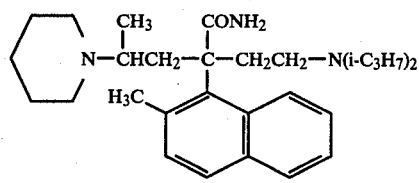

EXAMPLE 32

Substitution of an equivalent quantity of 4-(2-chloroethyl)morpholine for 2-chloro-N,N-diisopropylethylamine called for in Example 2, Method B affords, by the procedure detailed therein, α-(4-biphenylyl)-α-[2-(diisopropylamino)ethyl]-α-(2-morpholinoethyl)acetonitrile.

When an equivalent quantity of the preceding acetonitrile is substituted in the procedure of Example 4, there is obtained α-(4-biphenylyl)-α-[2-(diisopropylamino)ethyl]α-(2-morpholinoethyl)acetamide. This compound has the following structural formula

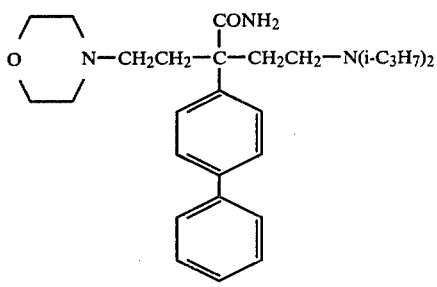

EXAMPLE 33

Substitution of an equivalent quantity of α-[2-(diisopropylamino)ethyl]-α-(1-naphthyl)acetonitrile and 1-(2-chloroethyl)-4-methylpiperazine in the procedure of Example 2, Method B, affords α-[2-(diisopropylamino)ethyl]α-[2-(4-methyl-1-piperazinyl)ethyl]-α-(1-naphthyl)acetonitrile.

When an equivalent quantity of the preceding acetonitrile is substituted in the procedure of Example 4, there is obtained α-[2-(diisopropylamino)ethyl]-α-[2-(4-methyl-1-piperazinyl)ethyl]-α-(1-naphthyl)acetamide. This compound has the following structural formula

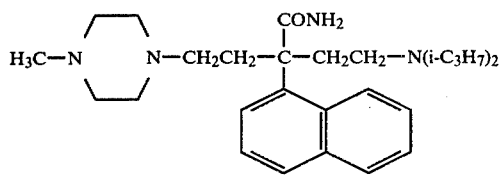

EXAMPLE 34

Substitution of an equivalent quantity of 1-(2-chloroethyl)piperazine for 2-chloro-N,N-diisopropylethylamine called for in Example 2, Method B, and substantial repetition of the procedure detailed therein, affords α-(4-biphenylyl)-α-[2-(diisopropylamino)ethyl]-α-[2-(1-piperazinyl)ethyl]acetonitrile.

When an equivalent quantity of the preceding acetonitrile is substituted in the procedure of Example 4, there is obtained α-(4-biphenylyl)-α-[2-(diisopropylamino)ethyl]-α-[2-(1-piperazinyl)ethyl]acetamide. This compound is represented by the following structural formula

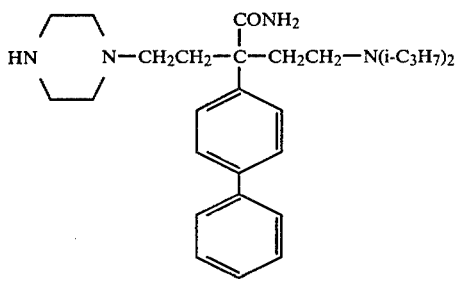

EXAMPLE 35

10 Parts of α,α-bis[2-(diisopropylamino)ethyl]-α-phenylacetamide is dissolved in 130 parts by volume of ethanol and the solution placed in pressure shaker with 1 part of ruthenium dioxide. Hydrogen is introduced at 1000 psi and the reaction mixture heated at about 125° C. and shaken for about 24 hours. Then, the reaction mixture is cooled to room temperature and filtered. The filtrate is stripped of solvent to give an oil. This oil is dissolved in methylene chloride, then hexane added to the solution, methylene chloride evaporated, and the hexane mixture cooled to give α-(cyclohexyl)-α,α-bis[2-(diisopropylamino)ethyl]acetamide, as a crystal solid melting at about 114°-115° C. This compound has the following structural formula

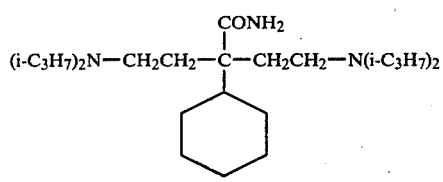

EXAMPLE 36

When an equivalent quantity of α-(4-biphenylyl)-α-[2-(diisopropylamino)ethyl]-α-(2-piperidinoethyl)acetamide is substituted in the procedure of Example 35, there is obtained α-(4-cyclohexylcyclohexyl)-α-[2-(diisopropylamino)ethyl]-α-(2-piperidinoethyl)acetamide. This compound has the following structural formula

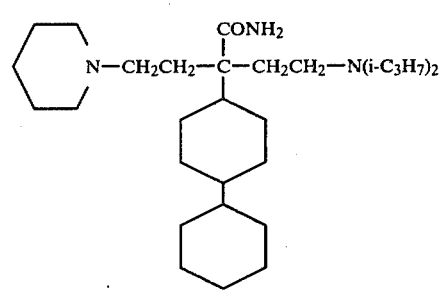

EXAMPLE 37

Substitution of an equivalent quantity of α-(o-tolyl)-α-[3-(diethylamino)propyl]acetonitrile for α-(4-biphenylyl)-α-[2-(diisopropylamino)ethyl]acetonitrile called for in Example 2, Method B and substantial repetition of the procedure detailed therein affords α-[3-(diethylamino)propyl]α-[2-(diisopropylamino)ethyl]-α-(o-tolyl)acetonitrile.

When an equivalent quantity of the above acetonitrile is substituted in the procedure of Example 4, there is obtained α-[3-(diethylamino)propyl]-α-[2-(diisopropylamino)ethyl]-α-(o-tolyl)acetamide. This compound has the following structural formula

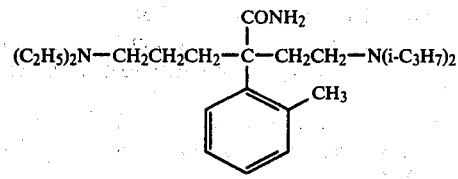

When an equivalent quantity of the above acetonitrile is substituted in the procedure of Example 35, there is obtained α-[3-(diethylamino)propyl]-α-[2-(diisopropylamino)ethyl]-α-(2-methylcyclohexyl)acetamide. This compound is represented by the following structural formula

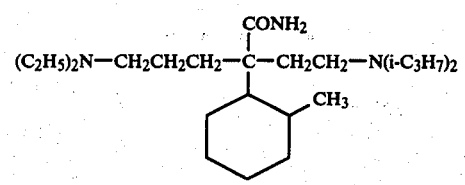

What is claimed is:
1. A compound of the formula

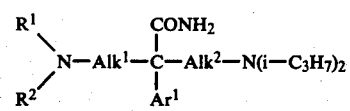

and the non-toxic pharmacologically acceptable acid addition salts thereof; wherein $R^1$ is lower alkyl having from 1 to 7 carbon atoms or cycloalkyl having 5 or 6 carbon atoms; $R^2$ is lower alkyl having from 1 to 7 carbon atoms; $Ar^1$ is biphenylyl, 1-or 2-naphthyl optionally substituted with halogen or lower alkyl having from 1 to 4 carbon atoms, or cycloalkyl having from 3 to 6 carbon atoms optionally substituted with lower alkyl having from 1 to 4 carbon atoms, or cyclohexyl and $Alk^1$ and $Alk^2$ are independently alkylene radicals having from 2 to 4 carbon atoms.

2. A compound according to claim 1 having the formula

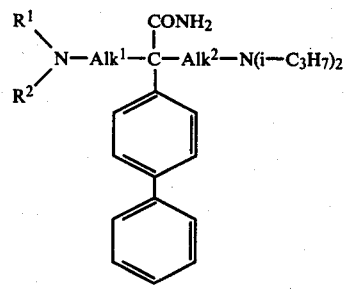

and the non-toxic pharmacologically acceptable acid addition salts thereof; wherein $R^1$ is lower alkyl having from 1 to 7 carbon atoms or cycloalkyl having 5 or 6 carbon atoms; $R^2$ is lower alkyl having from 1 to 7 carbon atoms; and $Alk^1$ and $Alk^2$ are independently alkylene radicals having from 2 to 4 atoms.

3. A compound according to claim 1 having the formula

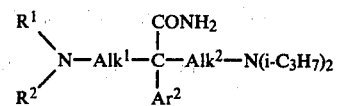

and the non-toxic pharmacologically acceptable acid addition salts thereof; wherein $R^1$ is lower alkyl having from 1 to 7 carbon atoms or cycloalkyl having 5 or 6 carbon atoms, $R^2$ is lower alkyl having from 1 to 7 carbon atoms; $Ar^2$ is 1-or 2-naphthyl optionally substituted with halogen or lower alkyl having from 1 to 4 carbon atoms; and $Alk^1$ and $Alk^2$ are independently alkylene radicals having from 2 to 4 carbon atoms.

4. A compound according to claim 1 having the formula

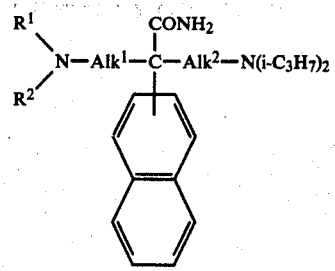

and the non-toxic pharmacologically acceptable acid addition salts thereof; wherein $R^1$ is lower alkyl having from 1 to 7 carbon atoms or cycloalkyl having 5 or 6 carbon atoms; $R^2$ is lower alkyl having from 1 to 7 carbon atoms; and $Alk^1$ and $Alk^2$ are independently alkylene radicals having from 2 to 4 carbon atoms.

5. A compound according to claim 1 having the formula

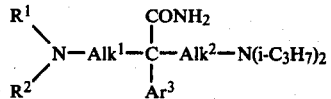

and the non-toxic pharmacologically acceptable acid addition salts thereof; wherein $R^1$ is lower alkyl having from 1 to 7 carbon atoms or cycloalkyl having 5 or 6 carbon atoms; $R^2$ is lower alkyl having from 1 to 7 carbon atoms; $Ar^3$ is cycloalkyl having from 3 to 6 carbon atoms optionally substituted with lower alkyl having from 1 to 4 carbon atoms, or cyclohexyl; and $Alk^1$ and $Alk^2$ are independently alkylene radicals having from 2 to 4 carbon atoms.

6. A compound according to claim 1 having the formula

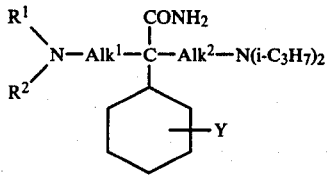

and the non-toxic pharmacologically acceptable acid addition salts thereof; wherein $R^1$ is lower alkyl having from 1 to 7 carbon atoms or cycloalkyl having 5 or 6 carbon atoms; $R^2$ is lower alkyl having from 1 to 7 carbon atoms; Y is hydrogen, cyclohexyl or lower alkyl having from 1 to 4 carbon atoms; and Alk$^1$ and Alk$^2$ are independently alkylene radicals having from 2 to 4 carbon atoms.

7. A compound according to claim 1 having the formula

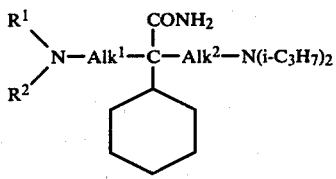

and the non-toxic pharmacologically acceptable addition salts thereof; wherein R$^1$ is lower alkyl having from 1 to 7 carbon atoms or cycloalkyl having 5 or 6 carbon atoms; R$^2$ is lower alkyl havings from 1 to 7 carbon atoms; and Alk$^1$ and Alk$^2$ independently are alkylene radicals having from 2 to 4 carbon atoms.

8. A compound according to claim 1 which is α-(4-biphenylyl)-α,α-bis[2-diisopropylamino)ethyl]acetamide.

9. A compound according to claim 1 which is α-(4-biphenylyl)-α-[2-(diisopropylamino)ethyl]-α-[2-(dimethylamino)ethyl]acetamide.

10. A compound according to claim 1 which is α,α-bis[2-diisopropylamino)ethyl]-α-(1-naphthyl)acetamide.

11. A compound according to claim 1 which is α,α-bis[2-(diisopropylamino)ethyl]-α-(2-naphthyl)acetamide.

12. A compound according to claim 1 which is α-cyclohexyl-α,α-bis[2-(diisopropylamino)ethyl]acetamide.

* * * * *